United States Patent
Weiss et al.

(10) Patent No.: US 7,340,301 B2
(45) Date of Patent: Mar. 4, 2008

(54) DEFIBRILLATOR SYSTEM

(75) Inventors: Teddy Weiss, Jerusalem (IL); Mendel Mendelbaum, Jerusalem (IL); Shraga Gorny, Jerusalem (IL); Iony Katz, Jerusalem (IL)

(73) Assignees: Hadasit Medical Research Services & Development Ltd., Jerusalem (IL); Yissum research Development Company of the Hebrew University, Jerusalem (IL)

( * ) Notice: Subject to any disclaimer, the term of this patent is extended or adjusted under 35 U.S.C. 154(b) by 456 days.

(21) Appl. No.: 10/482,362

(22) PCT Filed: Jun. 30, 2002

(86) PCT No.: PCT/IL02/00533

§ 371 (c)(1), (2), (4) Date: Jul. 20, 2004

(87) PCT Pub. No.: WO03/004094

PCT Pub. Date: Jan. 16, 2003

(65) Prior Publication Data

US 2004/0243185 A1 Dec. 2, 2004

(30) Foreign Application Priority Data

Jul. 3, 2001 (IL) .................................. 144120

(51) Int. Cl.
*A61N 1/39* (2006.01)

(52) U.S. Cl. ........................................................ 607/5
(58) Field of Classification Search ................ 607/5–8, 607/74; 361/1; 604/21
See application file for complete search history.

(56) References Cited

U.S. PATENT DOCUMENTS

| 3,566,876 | A | | 3/1971 | Stoft et al. |
| 3,808,502 | A | * | 4/1974 | Babilius .......................... 361/1 |
| 5,215,081 | A | * | 6/1993 | Ostroff ........................... 607/8 |
| 5,609,618 | A | * | 3/1997 | Archer .......................... 607/74 |
| 5,658,316 | A | | 8/1997 | Lamond et al. |
| 7,113,821 | B1 | * | 9/2006 | Sun et al. ...................... 604/21 |
| 2004/0143297 | A1 | * | 7/2004 | Ramsey .......................... 607/5 |

FOREIGN PATENT DOCUMENTS

EP   1 064 963 A1   1/2001

* cited by examiner

*Primary Examiner*—George Manuel
(74) *Attorney, Agent, or Firm*—Sughrue Mion, PLLC

(57) ABSTRACT

The invention provides a portable defibrillation system (2), including: a high voltage switch, and current control circuit (16) connectable to and fed by a power source (6); a high voltage transformer (14) fed by the current control circuit; a pair of electrode pads (12, 12') connected to the high voltage transformer, and a computer-based controller (18), operationally connected to the current control circuit, for governing the application of current to the high voltage transformer and, in turn, to the electrodes, wherein the high voltage applied to a patient by means of the electrode pads is directly derived from the power source.

10 Claims, 7 Drawing Sheets

Actual High Voltage Waveform

50Hz Rectified High Voltage Waveform

Modified 50Hz Rectified High Voltage Waveform

Pulse Width Generator Output

High Voltage Output Waveform

Required Energy is Achieved by Accumulation of Successive Decreasing Cycle Energy

DEFIBRILLATOR SYSTEM

FIELD OF THE INVENTION

The present invention relates to intensive care systems for the early treatment of sudden arrhythmias, and more particularly, to such systems which are suitable for domestic or outpatient use by non-medical personnel, on a dying patient.

BACKGROUND OF THE INVENTION

Heretofore, sudden cardiac death caused by ventricular fibrillation or cardiac arrest, was the major cause of death among the adult population in developed countries. Ventricular fibrillation can be halted and normal heart activity restored, by the electrical defibrillation procedure, comprising an electric shock applied to the heart. Similarly, heart arrest can be treated by pacing electrical signals, that is, a pulse train, at the rate of 60-80 pulses per minute. The defibrillation procedure is usually effective when applied in intensive care units in hospitals, where a state of fibrillation is easily detected and treatment is quickly applied. Hospital intensive care units are usually equipped with expensive defibrillation equipment, along with professional personnel who are able to perform the treatment.

The above considerations also apply to the state of heart arrest and the use of an external pacemaker device. Thus, while the description of the present invention relates to defibrillators, it should be understood that it is also meant to include pacemaker systems.

It is of paramount importance that a defibrillation procedure be done immediately; otherwise, irreversible, irreparable damage is caused. The patient's brain is be damaged within minutes of the start of fibrillation, due to a lack of oxygen supply, and all other organs will stop functioning. Early defibrillation restores cardiac function and spontaneous respiration, avoiding anoxic brain damage. In addition, there is a clear linkage between the elapsed time between the beginning of ventricular fibrillation, the beginning of the defibrillation procedure, and the procedure's success.

The majority of potential fibrillation victims live at home, however, and are not under constant medical supervision. This is even more so with the modern trend towards treatment of patients at home. These people cannot be given immediate defibrillation treatment, for several reasons:

1) From the moment that the victim of ventricular fibrillation loses consciousness, it will take at least from 10-20 minutes until the mobile care unit reaches him. Therefore, in such cases defibrillation is usually not successful and irreversible cardiac damage is caused; if the patient survives, he will remain in coma with permanent brain damage.
2) Presently used defibrillation equipment is expensive, costing in the range of thousands of dollars. The majority of the people cannot afford to include such equipment as part of their home first aid kits.
3) Much of the presently used defibrillation equipment must be operated by professional, trained medical personnel, who diagnose the case as fibrillation, find the right equipment, and use it correctly to apply electric shock at the proper location. Non-professional people are unfamiliar with such equipment; and moreover, they tend to panic and be ineffective in an emergency situation. Therefore, family members and neighbors usually cannot be relied upon to perform defibrillation treatment.
4) The defibrillation equipment has to be kept in good operating condition so that it will be ready for use in an emergency. Hospital maintenance teams routinely keep all equipment in good condition and perform required periodical tests and repairs. It is difficult, however, to keep complex defibrillation equipment in good condition at home and to do the required testing and repairs.
5) Defibrillation equipment may be dangerous if misused. High voltages generated by the equipment can endanger its operators, children, or other non-professionals. The existing equipment lacks the safety devices which are required for home use.

SUMMARY OF THE INVENTION

It is therefore an object of the present invention to overcome the above-mentioned problems and to provide a low-cost, automatic defibrillation system utilizing available alternating current, for treating fibrillation and cardiac arrest patients at home.

Thus, the invention provides a portable defibrillation system, comprising a high voltage switch and current control circuit connectable to and fed by a power source; a high voltage transformer fed by said current control circuit; a pair of electrode pads connected to the high voltage transformer, and a computer-based controller, operationally connected to the current control circuit, for governing the application of current to the high voltage transformer and, in turn, to the electrodes, wherein the high voltage applied to a patient by means of the electrode pads is directly derived from the power source.

BRIEF DESCRIPTION OF THE DRAWINGS

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is a block diagram of the defibrillation system according to the present invention;

FIG. 2 is a circuit diagram of a first embodiment of the invention;

FIG. 3 depicts graphs showing the waveforms produced at different points in the circuit of FIG. 2;

FIG. 4 is a circuit diagram of a second embodiment of the invention;

FIG. 5 depicts graphs showing the waveforms produced at different points in the circuit of FIG. 4;

FIG. 6 is a circuit diagram of another embodiment of the invention, and

FIG. 7 depicts graphs showing the waveforms produced at different points in the circuit of FIG. 6.

DETAILED DESCRIPTION

Figure 1:
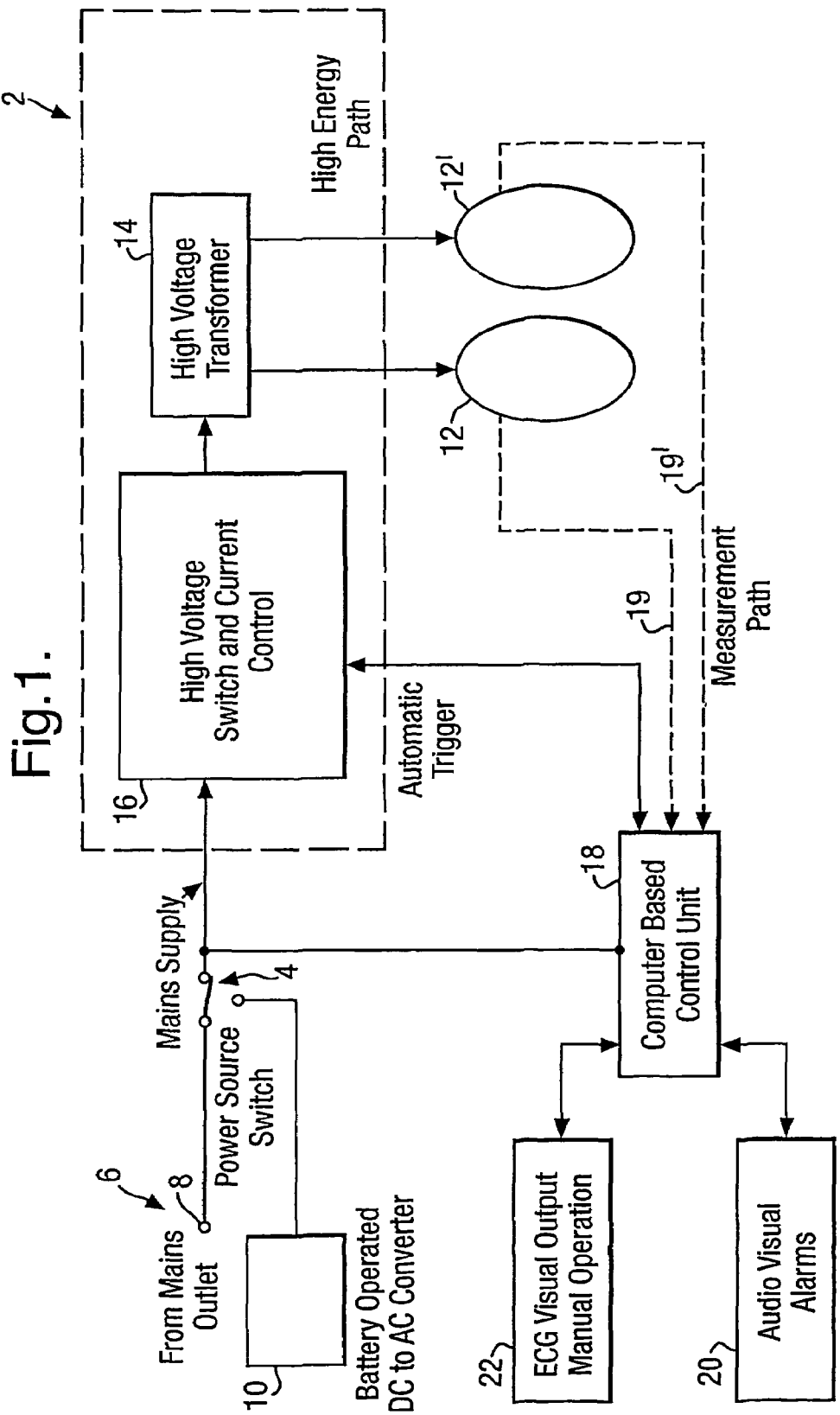

Referring now to FIG. 1, there is shown a block diagram of an automatic defibrillation system 2 according to the present invention. System 2 is connectable, via switch 4, to a common power source 6, e.g., AC mains outlet 8 or, alternatively, to a battery-operated DC-to-AC converter 10, for use when mains power is not available.

System 2 includes a pair of electrodes 12, 12' electrically connected to, and fed by, a high voltage output transformer 14, e.g., a step-up transformer, receiving power from source 6 via a high voltage switch and current control circuit 16. The latter is governed by computer-based controller 18. Advantageously, measurement leads 19, 19' connect electrodes 12, 12' to the computer-based controller 18. The system may be optionally furnished with an audio-visual alarm 20 and an ECG visual output manual operation unit 22.

Figure 2:
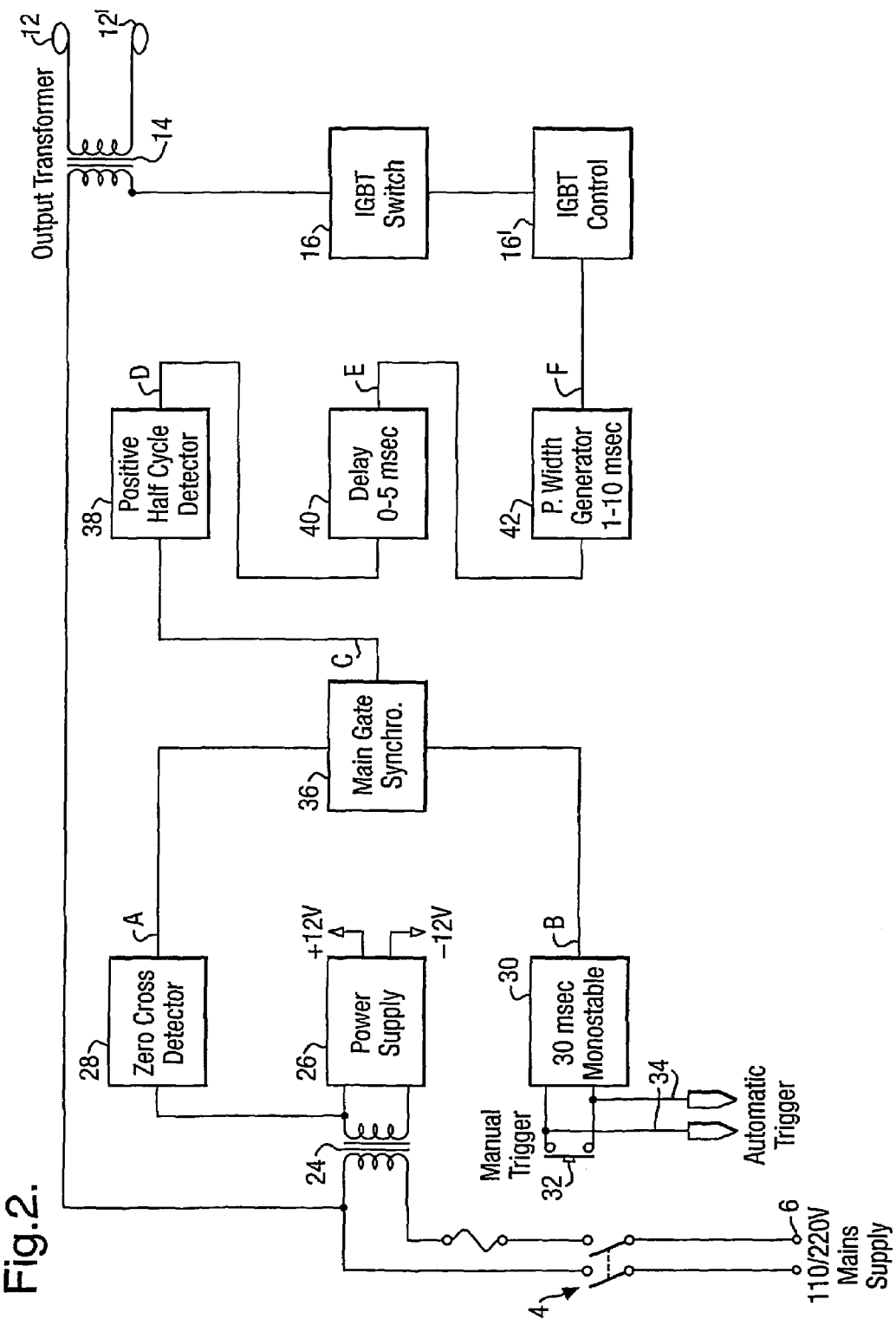

FIG. 2 illustrates a first embodiment of the invention. System 2 is connectable via switch 4 to the mains power source 6. A step-down transformer 24 feeds a power supply 26, providing the required DC voltage to the system. A zero cross detector 28 is connected to the low-voltage side of transformer 24, and detects the exact timing of the zero crossing of the mains sine wave, to be used as a reference for the operation of the system. A monostable 30, e.g., a 30 msec monostable, is either manually triggered by push button 32 or automatically through leads 34 to a computer (not shown) for analyzing the ECG signals of a patient. The computer is connected to a main gate synchronizer 36, which synchronizes between the input signals arriving from the zero crossing detector 28 and the signals arriving from the monostable 30. The output from main gate synchronizer 36 is fed to a positive half-cycle detector 38, for detecting the beginning of a first positive half-cycle of the mains occurring in response to manual or automatic triggering.

As a first part of the procedure for controlling the power that will be transferred through the output transformer 14 to the electrodes 12, 12', circuit 40 enables a time delay of, e.g., 0 to 5 msec, counted from the zero crossing of the sine wave. This delay marks the beginning of the pulse of energy transferred to the patient. The second part of the power-controlling procedure comprises generating a pulse in generator 42, e.g., 1 to 10 msec wide, according to the amount of energy that has to be transferred to transformer 14 and thence, via electrodes 12, 12', to the patient.

The high voltage switch and current control 16 can be divided into two components: IGBT control 16', which transforms the logic levels used in the other parts of the system to the levels required to trigger the high current IGBT switch 16". The latter is a high power switch supplying the primary of high voltage transformer 14 with an adequate waveform, shaped by pulse width generator 42.

Figure 3:
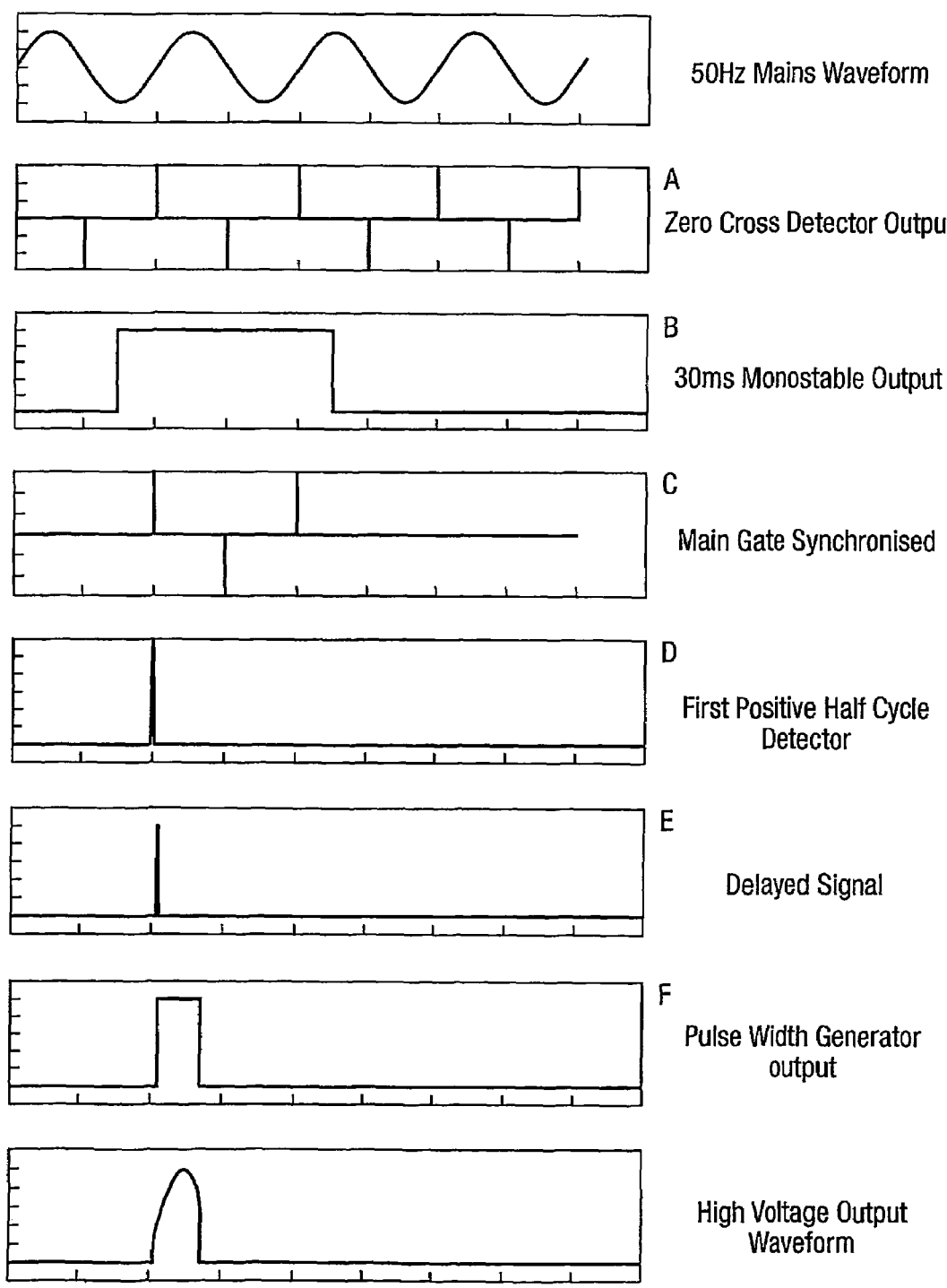

Referring now also to FIG. 3, the system's waveforms are shown in alignment, including the mains waveform A, the zero cross output signal B, monostable 30 output signal C, main gate 36 synchronizing signal D, first positive half-cycle signal E, delay signal F, pulse width waveform G at the output of the pulse width generator 42, and the actual high voltage output waveform H, which is applied to electrodes 12, 12'.

Thus, from the synchronized signal, the zero crossing pulse preceding the first positive half-cycle is selected and used as a triggering signal for the generation of a pulse whose beginning timing and end timing can be controlled in order to ensure that the required amount of energy is transferred to the patient. This pulse is, in turn, used as a gating signal to the high current switch applying the mains' power to the step-up output transformer 14, used to obtain the required high voltage to be applied to the patient's chest.

Figure 4:
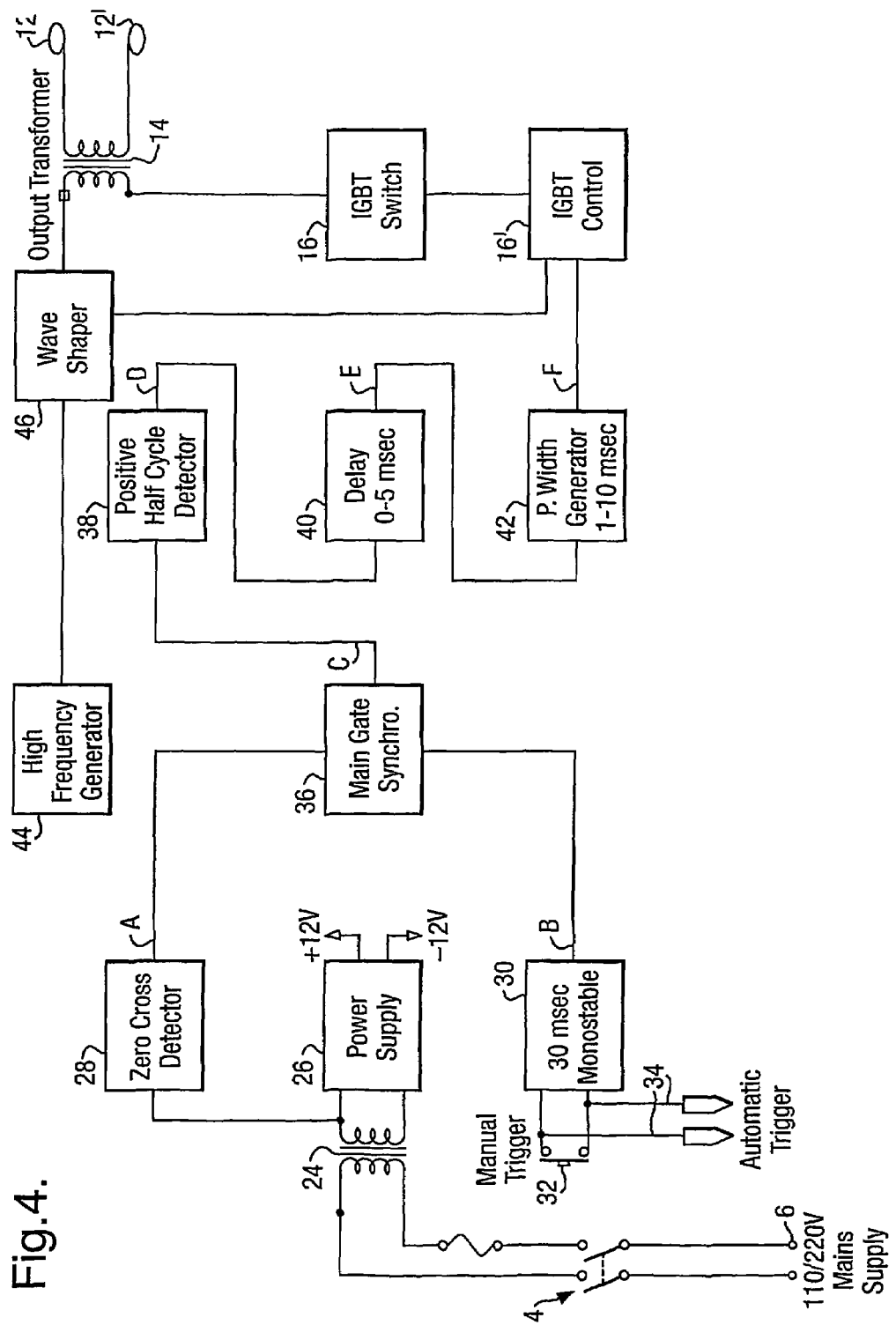
Figure 5:
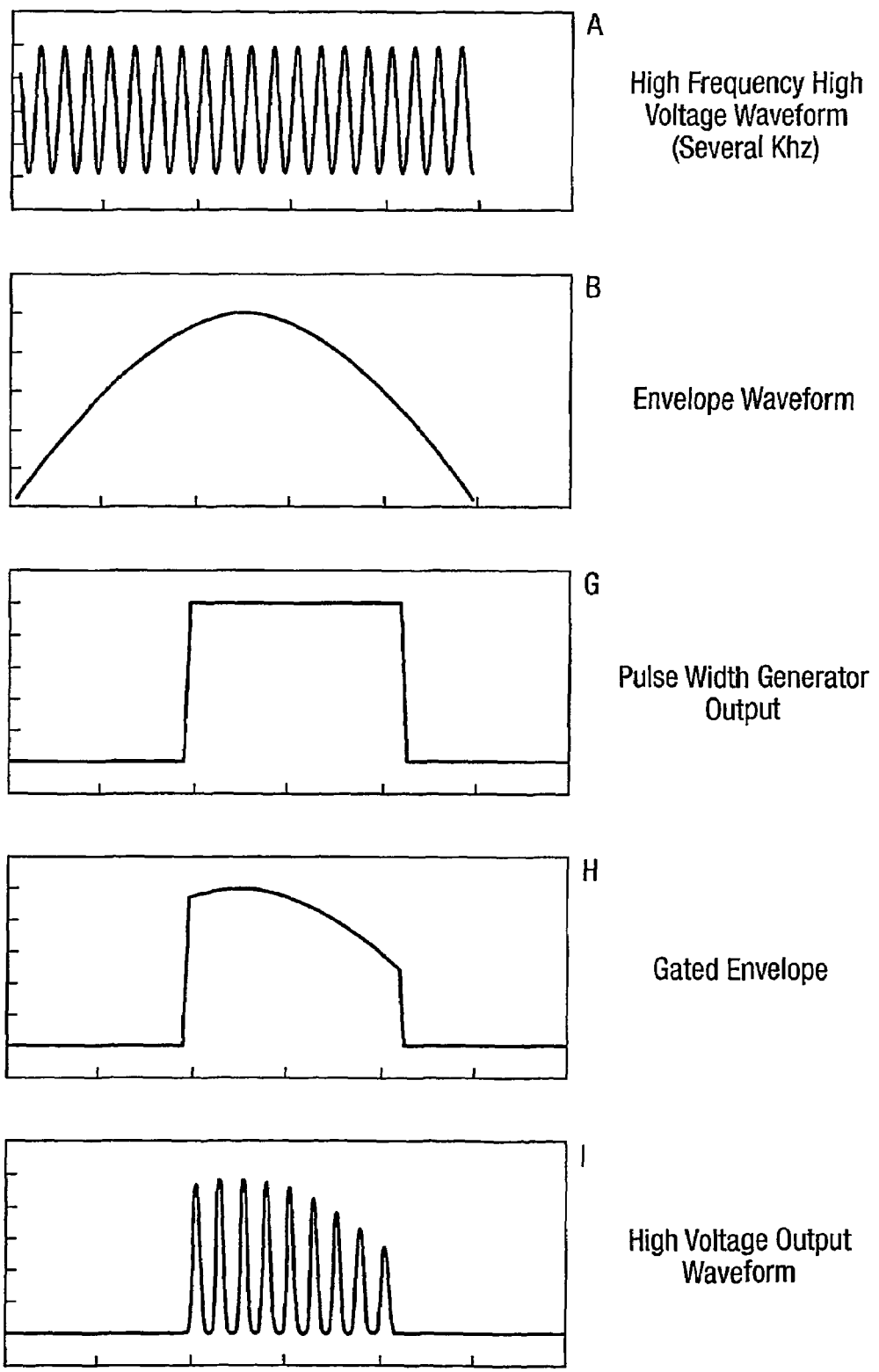

FIGS. 4 and 5 depict a modification of the embodiment of FIGS. 2 and 3, in which there is provided a high frequency generator 44 for providing a train of high frequency (A, FIG. 5), e.g., a 12 to 24 KHz sinusoidal waveform B, to be used as a power source for the step-up output transformer 14. After passing through a wave shaper 46, the pulses are shaped as shown at H. The high voltage output applied to the patient is thus shown as I of FIG. 5. The wave shaper 46 enables the application of consecutive pulses shaped according to the requirements within limits of less than 200 ms delay, in contrast with known systems based on capacitor discharge where it takes several seconds before a second discharge is possible.

Furthermore, the wave shaper enables the application of pulses shaped according to any requirements, within limits of the sine wave, having variable peak outputs and starting and stopping at will, creating a mono or biphasic waveform, or continuous wave composed of two or more segments, thereby enabling the delivery of the exact amount of energy required.

Figure 6:
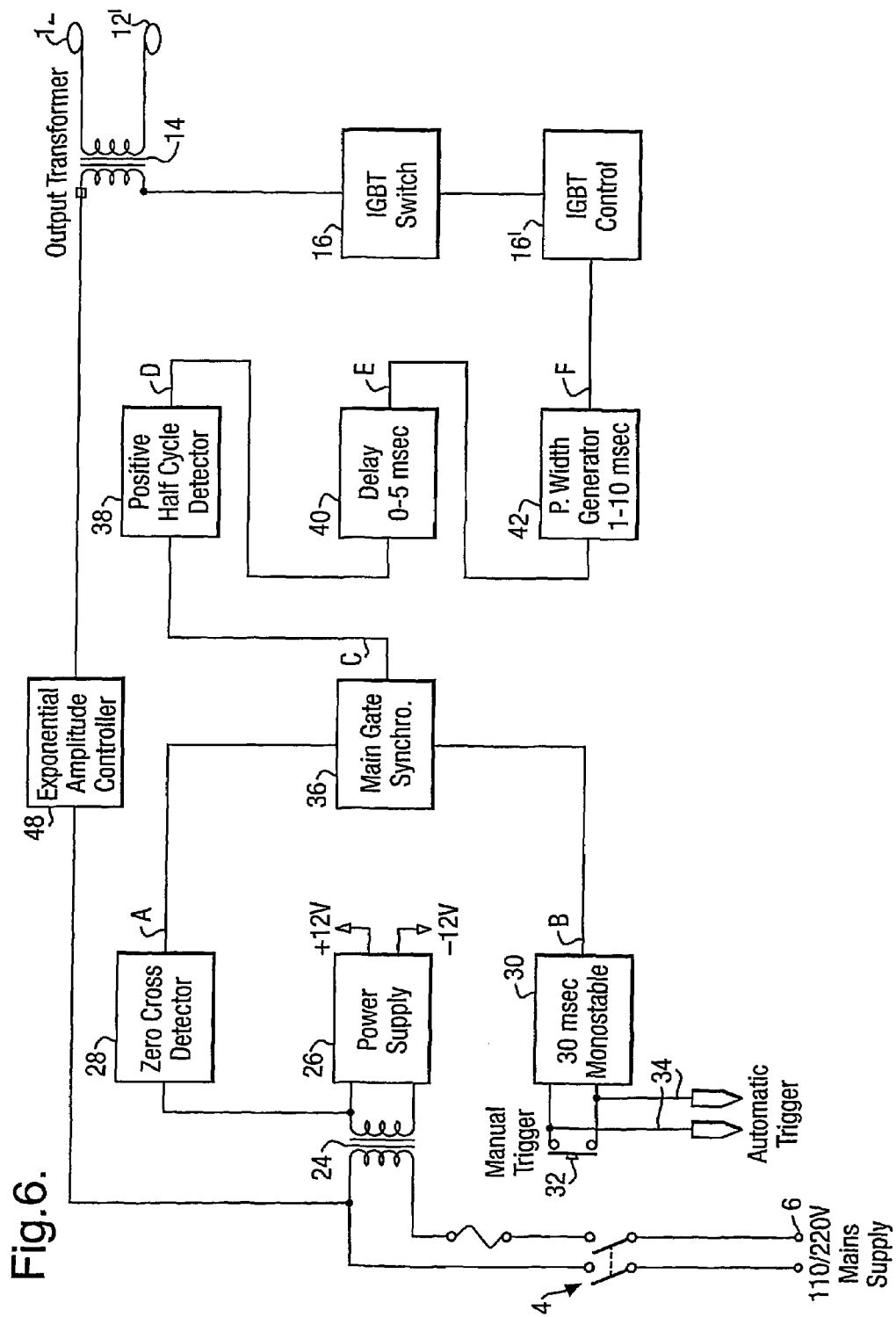
Figure 7:
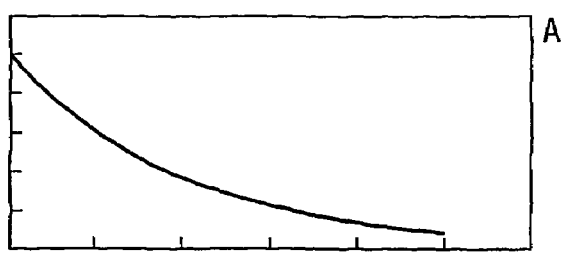
Figure 7:
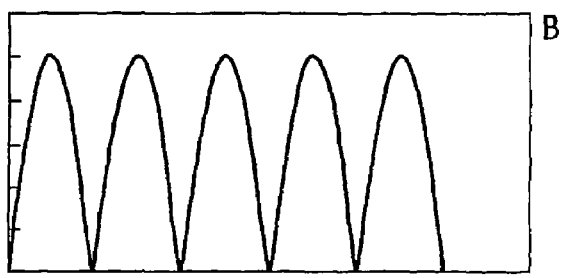
Figure 7:
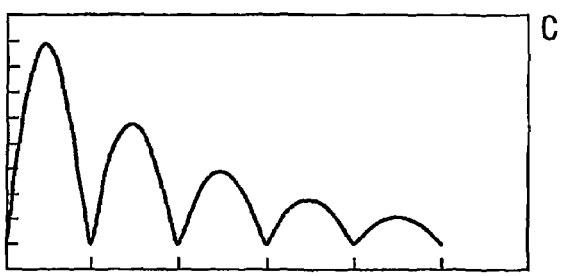
Figure 7:
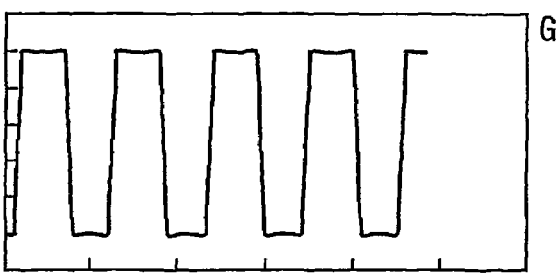
Figure 7:

A further embodiment is shown in FIGS. 6 and 7. Accordingly, an exponential amplitude controller 48 is connected in circuit between the mains and the output transformer 14. The controller 48 is used to control the amplitude (A, FIG. 7) of the sinusoidal waveform obtained by the mains (B, FIG. 7), resulting in a progressively reduced high voltage waveform C. Amplitude decrease is calculated by the system in such a way that the accumulated energy transferred to the patient reaches the required value determined by the patient's condition and other, per se known, considerations.

It will be evident to those skilled in the art that the invention is not limited to the details of the foregoing illustrated embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A portable defibrillation system, comprising:
    a high voltage switch and current control circuit connectable to and fed by an AC power source;
    a high voltage transformer fed by said current control circuit;
    a pair of electrode pads connected to said high voltage transformer, and
    a computer-based controller, operationally connected to said current control circuit, for governing the application of current to said high voltage transformer and, in turn, to said electrodes;
    wherein the high voltage applied to a patient by means of said electrode pads is directly derived from said AC power source.

2. The portable defibrillation system as claimed in claim 1, further comprising measurement leads connecting said electrodes with said computer-based controller.

3. The portable defibrillation system as claimed in claim 1, wherein said AC power source is selected from the group consisting of a mains AC power outlet and a battery-operated DC to AC converter.

4. The portable defibrillation system as claimed in claim 1, further comprising an audio-visual alarm connected to said computer-based controller.

5. The portable defibrillation system as claimed in claim 1, further comprising an ECG visual output manual operation connected to said computer.

6. The portable defibrillation system as claimed in claim 1, wherein said computer-based controller is connected to said power source via a zero crossing detector for establishing a system operation reference.

7. The portable defibrillation system as claimed in claim 6, further comprising a main gate synchronizer connected to said zero crossing detector and a patient's ECG signal.

8. The portable defibrillation system as claimed in claim 1, further comprising a wave shaper for shaping voltage pulses produced by said high voltage transformer.

9. The portable defibrillation system as claimed in claim 8, wherein said wave shaper is capable of application of pulses with a variable peak output voltage facilitating delivery of an exact amount of energy required.

10. The portable defibrillation system as claimed in claim 1, further comprising an exponential amplitude controller connected in circuit between said power source and said high voltage transformer.

* * * * *